United States Patent [19]
Schneider et al.

[11] Patent Number: 5,276,207
[45] Date of Patent: Jan. 4, 1994

[54] PROCESS FOR PREPARING 1-[/2S/-METHYL-3-MERCAPTO-PROPIONYL]-PYRROLIDINE-/2S/-CARBOXYLIC ACID

[75] Inventors: Géza Schneider; Gábor Blaskó; Ágnes Kovács née Palotai; Gabriella Ürmös née Lassú; Ilma Dinnyés née Nagy; Iván Beck; Elemér Jákfalvi; András Dietz, all of Budapest, Hungry

[73] Assignee: Egis Gyogyszergyar Rt., Budapest, Hungary

[21] Appl. No.: 25,413

[22] Filed: Mar. 1, 1993

[30] Foreign Application Priority Data

Mar. 13, 1992 [HU] Hungary .................. P 92 00837

[51] Int. Cl.[5] .................................... C07D 207/16
[52] U.S. Cl. .................................... 548/533
[58] Field of Search ........................ 548/533

[56] References Cited
U.S. PATENT DOCUMENTS
5,202,443  4/1993  Schneider et al. .................. 548/533

Primary Examiner—Joseph Paul Brust
Attorney, Agent, or Firm—Beveridge, Degrandi, Weilacher & Young

[57] ABSTRACT

The invention relates to a novel process for preparing 1-[/2S/-methyl-3-mercaptopropionyl]-pyrrolidine-/2S/-carboxylic acid of the formula I $$HS-CH_2-\underset{CH_3}{\underset{|}{CH}}-CO-N\begin{array}{c}(S)\\ \\ (S)\\COOH\end{array} \quad (I)$$

in which 1-[/2S/-methyl-3-thiocyanatopropionyl]-pyrrolidine-/2S/-carboxylic acid of the formula II $$NCS-CH_2-\underset{CH_3}{\underset{|}{CH}}-CO-N\begin{array}{c}(S)\\ \\ (S)\\COOH\end{array} \quad (II)$$

is dissolved in an aqueous mineral acid, the solution obtained is diluted with water and the 1-[/2S/-methyl-3-carbamoylthiopropionyl]-pyrrolidine-/2S/-carboxylic acid of the formula III $$NH_2\overset{O}{\overset{\|}{C}}S-CH_2-\underset{CH_3}{\underset{|}{CH}}-CO-N\begin{array}{c}(S)\\ \\ (S)\\COOH\end{array} \quad (III)$$

that forms is hydrolized with an aqueous solution of a base.

7 Claims, No Drawings

PROCESS FOR PREPARING 1-[/2S/-METHYL-3-MERCAPTO-PROPIONYL]-PYRROLIDINE-/2S/-CARBOXYLIC ACID

The invention relates to a novel process for preparing 1-[/2S/-methyl-3-mercaptopropionyl]-pyrrolidine-/2S/-carboxylic acid of the formula I

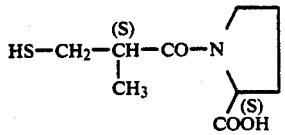

The compound of the formula I is known under the international non-proprietary name captopril as a potent antihypertensive drug.

Several processes are known for the preparation of the compound of the formula I. A common feature of the major part of them consists in that, at first, a 2-methylpropionyl-pyrrolidine-/2S/-carboxylic acid derivative comprising the mercapto group in a protected or masked form is prepared, then the protective group is removed or the masked group is converted to the free mercapto group to obtain captopril. In the processes of course, the desired /2S,2S/ diastereoisomer is to be separated. Thus, according to U.S. Pat. No. 4,105,776 or a publication [Biochemistry, 16, 5484 /1977/] dealing with one of the process variants described therein in more detail, L-proline is transformed to tertiary-butyl L-prolinate which is acylated with 3-acetylthio-2-methylpropionic acid in the presence of N,N'-dicyclohexyl-carbodiimide, then the acylated product is resolved through its dicyclohexylamine salt, 1-[/2S/-methyl-3-acetylthiopropionyl]-pyrrolidine-/2S/-carboxylic acid is separated and finally the protective group is removed by hydrolysis. The overall yield calculated for L-proline is only about 10 per cent.

According to U.S. Pat. No. 4,332,725 L-proline is acylated with a 3-halo-2-methylpropionyl chloride, the desired 1-[/2S/-methyl-3-halopropionyl]-pyrrolidine-/2S/-carboxylic acid diastereoisomer is directly separated and reacted with an alkali metal thiosulfate, then the Bunte's salt obtained is hydrolized with an acid to obtain captopril. In this way, an overall yield of about 30 per cent calculated for L-proline is achieved.

The Austrian Patent Specification No. 387,381 describes the reaction of 1-[/2S/-methyl-3-halopropionyl]-pyrrolidine-/2S/-carboxylic acid with thiourea to give the corresponding isothiuronium derivative which is then hydrolyzed to captopril, resulting in an overall yield of 34 to 35 per cent calculated for L-proline.

The aim of the invention was to provide a process for the preparation of captopril which renders possible to produce the compound in a simple way with a yield over 50 per cent calculated for L-proline.

Now it has been found that the above aim can be achieved by the process of the invention in which 1-[/2S/-methyl-3-thiocyanatopropionyl]-pyrrolidine-/2S/-carboxylic acid of the formula II

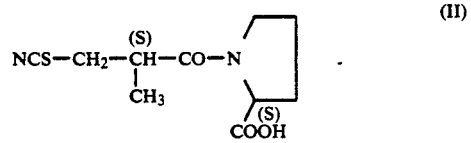

is dissolved in an aqueous mineral acid, the solution obtained is diluted with water and the 1-[/2S/-methyl-3-carbamoylthiopropionyl]-pyrrolidine-/2S/-carboxylic acid of the formula III

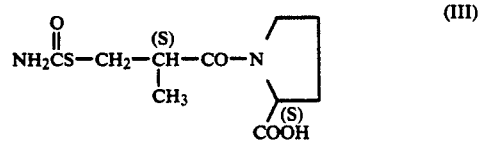

that forms is hydrolized with an aqueous solution of a base.

The mineral acid used for the dissolution of the compound of the formula II is preferably aqueous sulfuric acid, however, aqueous hydrochloric acid or aqueous hydrogen bromide can be employed, too. In general, 40 to 98 per cent by mass of aqueous sulfuric acid, 30 to 36 per cent by mass of aqueous hydrochloric acid or 30 to 70 per cent by mass of aqueous hydrogen bromide is used.

1-[/2S/-Methyl-3-thiocyanatopropionyl]-pyrrolidine-/2S/-carboxylic acid of the formula II is dissolved in the aqueous mineral acid at a temperature of 0° to 70° C., in general. The solution obtained is diluted suitably with cold water and/or ice, the amount of which is equivalent to 0.2 to 10 times the amount of the original solution. Then, 1-[/2S/-methyl-3-carbamoylthiopropionyl]-pyrrolidine-/2S/-carboxylic acid of the formula III precipitates. The precipitate can be separated for instance by filtration or, preferably, it is hydrolized without separation. The hydrolysis is performed with an aqueous solution of a base such as sodium hydroxide, potassium hydroxide or ammonia, suitably at a temperature of 0° to 70° C. It is preferred to employ aqueous ammonia containing 5 to 30 percent by mass of ammonia. Sodium hydroxide or potassium hydroxide is employed in most cases at a concentration of 5 to 40 percent by mass.

It is preferred to exclude the oxygen content of the air during the hydrolysis, for example by introducing nitrogen into the reaction vessel.

The captopril formed is separated by using common methods of the preparative organic chemistry. Preferably, after the hydrolysis, the reaction mixture is made acidic by the addition of for example aqueous hydrochloric acid and the captopril precipitated is filtered or extracted with an organic solvent.

1-[/2S/-Methyl-3-thiocyanatopropionyl]-pyrrolidine-/2S/-carboxylic acid of the formula II used as the starting substance in the process of the invention is a novel compound which is prepared by the acylation of L-proline with a reactive acylating derivative of /2S/-methyl-3-thiocyanatopropionic acid of the formula IV

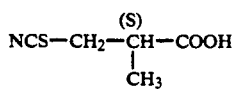

Suitable reactive acylating derivatives are the mixed anhydrides of the general formula VI

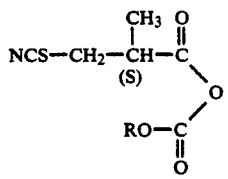

wherein R stands for a $C_{1-5}$ alkyl or benzyl group.

The mixed anhydrides of the general formula VI are prepared by reacting /2S/-methyl-3-thiocyanatopropionic acid of the formula IV with a chloroformate ester of the general formula V

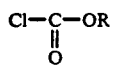

wherein R is as defined above, in the presence of an acid binding agent.

/2S/-Methyl-3-thiocyanatopropionic acid of the formula IV is prepared by reacting an isobutyric acid derivative of the general formula VII

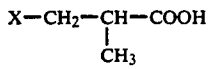

wherein X stands for an $R^1$—$SO_2$—O— group containing a $C_{1-4}$ alkyl or a phenyl moiety optionally substituted with a methyl group as $R^1$, with a rhodanide of the general formula VIII

wherein A represents an alkali metal or an alkali earth metal atom or a group of the general formula a

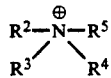

wherein $R^2$, $R^3$, $R^4$ and $R^5$ represent, independently, hydrogen, $C_{1-4}$ alkyl or benzyl group, then resolving the racemic 2-methyl-3-thiocyanatopropionic acid formed.

The resolution of 2-methyl-3-thiocyanatopropionic acid is preferably performed by using /S/-1-phenylethylamine.

By using the process of the invention a yield of about 95 per cent can be realized. Therefore, the overall yield calculated for L-proline is about 57 per cent. Thus, the process of the invention is considerably more economical than the known processes of the prior art; it consists of only a low number of reaction steps to give captopril of very high purity.

The process of the invention is further illustrated in detail by the following non-limiting Examples.

EXAMPLE 1

1-[/2S/-Methyl-3-mercaptopropionyl]-pyrrolidine-/2S/-carboxylic acid 12.5 ml of concentrated sulfuric acid are diluted with 12.5 ml of water. To the solution obtained 24.23 g of 1-[/2S/-methyl-3-thiocyanatopropionyl]-pyrrolidine-/2S/-carboxylic acid are added at 20° C. in 10 to 20 minutes. The reaction mixture is stirred for an hour while maintaining the temperature below 40° C. by cooling as required. A pale yellow, viscous solution is obtained which is kept at 20° to 25° C. for 4 hours. Then, 25 g of crushed ice are added to the solution. The suspension of the crystals formed is stirred at 0° to 5° C. for 15 minutes, then 100 ml of 25 per cent by mass of aqueous ammonia are added under cooling at a rate that the reaction temperature remains under 50° C. During the addition of aqueous ammonia nitrogen gas is introduced continously to the reaction vessel. The solution obtained is kept at 50° to 55° C. for 3 hours, then cooled to 20° C., 100 ml of dichloromethane are added and the pH of the mixture is adjusted to a value of 1 by the addition of concentrated aqueous hydrochloric acid. The mixture is stirred for some minutes, then the aqueous phase is separated and extracted four times with dichloromethane using 50 ml of solvent each time. The organic solutions are combined, washed with 25 ml of 0.1 n hydrochloric acid, twice with 25 ml of water, dried over anhydrous magnesium sulfate and evaporated. The residue is dissolved in 80 ml of ethyl acetate, the solution obtained is concentrated under reduced pressure to a volume of 40 ml and cooled to 0° C., then left at this temperature for a night. The crystals formed are filtered under nitrogen and washed with cold ethyl acetate. Thus, 20.27 g /93.3%/ of the title product are obtained, m.p.: 106°-108° C.; $[\alpha]_D^{25} = -132°$ /c=0.5; ethanol/.

EXAMPLE 2

A/

1-[/2S/-Methyl-3-carbamoylthiopropionyl]-pyrrolidine-/2S/-carboxylic acid 12.5 ml of concentrated sulfuric acid are diluted with 12.5 ml of water. To the solution obtained and cooled to 20° C. 24.23 g of 1-[/2S/-methyl-3-thiocyanatopropionyl]-pyrrolidine-/2S/-carboxylic acid are added in 10 to 20 minutes. The reaction mixture is stirred for an hour while maintaining the temperature under 40° C. by cooling as required. The same applies to the addition of the thiocyanato compound. A pale yellow, viscous solution is obtained which is kept at 20° to 25° C. for 4 hours. 25 g of crushed ice are added to the solution and the crystal mass is left to stand at 0° C. for a night. Then the crystals are separated by filtration, washed twice with 10 ml of ice water and 3 times with 10 ml of diisopropyl ether. 24,78 g /95.2%/ of the title compound are obtained, m.p.: 152°-153° C.; $[\alpha]_D^{20} = -204°$ /c=0.5; water/.

IR spectrum /KBr/: $\nu_{CO} = 1667$ cm$^{-1}$ /—SCONH$_2$/.

B/

1-[/2S/-Methyl-3-mercaptopropionyl]-pyrrolidine-/2S/-carboxylic acid 26.03 g of 1-[/2S/-methyl-3-carbamoylthiopropionyl]-pyrrolidine-/2S/-carboxylic acid prepared as described above are added to 80 ml of 25 per cent by mass of aqueous ammonia under stirring and introducing nitrogen gas while maintaining the temperature under 30° C. The solution obtained is stirred at 50° to 55° C. for 3 hours, then cooled to 20° C., 100 ml of dichloromethane are added and the pH of the mixture is adjusted to a value of 1 by the addition of concentrated aqueous hydrochloric acid. The mixture is stirred for some minutes, then the aqueous phase is separated and extracted four times with 50 ml dichloromethane. The organic solutions are combined, washed with 25 ml of 0.1 n hydrochloric acid, twice with 25 ml of water, dried over anhydrous magnesium sulfate and evaporated. The residue is dissolved in 80 ml of ethyl acetate, the solution obtained is concentrated under reduced pressure to a volume of 40 ml and cooled to 0° C., then left at this temperature for a night. The crystals formed are filtered under nitrogen and washed with cold ethyl acetate. Thus, 20.25 g /93.2%/ of the title compound are obtained, m.p.: 106°-108° C.; $[\alpha]_D^{25} = -132°$ /c=0.5; ethanol/.

EXAMPLE 3

1-[/2S/-Methyl-3-mercaptopropionyl]-pyrrolidine- /2S/-carboxylic acid

One proceeds as described in Example 1 with the difference that the product is separated by filtration after adjusting the pH of the mixture to a value of 1 to give 18.68 g /85.9%/ of the title compound, m.p.: 105°-106° C.; $[\alpha]_D^{25} = -130°$ /c=0.5; ethanol/.

EXAMPLE 4

1-[/2S/-Methyl-3-mercaptopropionyl]-pyrrolidine- /2S/-carboxylic acid

One proceeds as described in Example 1 with the difference that the starting compound is dissolved in 95 per cent by mass sulfuric acid. 19.67 g /90.5%/ of the title compound are obtained, m.p.: 105°-106° C.; $[\alpha]_D^{25} = -130°$ /c=0.5; ethanol/.

EXAMPLE 5

1-[/2S/-Methyl-3-mercaptopropionyl]-pyrrolidine- /2S/-carboxylic acid

One proceeds as described in Example 1 with the difference that the starting compound is dissolved in 42 per cent by mass hydrogen chloride. 15.42 g /71%/ of the title compound are obtained, m.p.: 105°-106° C.; $[\alpha]_D^{25} = -130°$ /c=0.5; ethanol/.

Preparation of the starting compound

2-Methyl-3-thiocyanatopropionic acid 16.7 g of 2-methyl-3-bromopropionic acid are dissolved in 50 ml of toluene, the solution obtained is cooled to 0° C., then 19.42 g of potassium rhodanide and 5 ml of water are added. The pH value of the reaction mixture is adjusted to 6.5 by the dropwise addition of 10 n sodium hydroxide. The pale yellow biphasic solution obtained is stirred at 25° C. for 48 hours while maintaining the pH value between 6.4 and 6.6 by adding further amounts of sodium hydroxide as required. The reaction mixture is cooled to 0° C. and adjusted to a pH value of 2.7 by adding 10 n sulfuric acid, then filtered and the organic phase is separated. The aqueous phase is extracted 5 times with 20 ml of toluene, the organic solutions are combined and extracted with 10 ml of water. The pale yellow toluene solution is dried over anhydrous magnesium sulfate and evaporated under reduced pressure to obtain 11.13 g /76.7%/ of 2-methyl-3-thiocyanatopropionic acid, m.p.: 24°-25° C. Based on determination by gas chromatography, the purity of the product is 98 to 99 per cent.

IR spectrum /film/: $v_{NCS} = 2157$ cm$^{-1}$.

/2S/-Methyl-3-thiocyanatopropionic acid

A/ /2S/-Methyl-3-thiocyanatopropionic acid /αS/-methylbenzomethane amine salt 14.52 g of γacemic 2-methyl-3-thiocyanatopropionic acid are dissolved in 20 ml of toluene and to the solution obtained a solution of 8.48 g of /αS/-methylbenzomethane amine in 16.5 ml of toluene is added, drop by drop, in 5 minutes under stirring. During the addition the reaction temperature rises from 26° C. to 46° C. The pale yellow solution obtained is maintained at 50° C. for 1 hour, then cooled to 25° C. and 1.33 g of the title salt are added to seed the solution. The crystal mass is stirred at 0° C. for 1 hour, then filtered, washed 3 times with 10 ml of cold toluene each and dried to give 10.91 g /72%/ of the title salt, m.p.: 90.2°-91.8° C.; $[\alpha]_D^{25} = -54.8°$/c=1; water/. The optical purity of the salt is 93 percent.

The resolution procedure is repeated to obtain the title salt having an optical purity of 99 percent. M.p.: 92°-94° C.

B/ /2S/-Methyl-3-thiocyanatopropionic acid 26.63 g of a twice resolved salt obtained as described under A/ above are dissolved in 100 ml of water, then 100 ml of ethyl acetate are added. The mixture having two phases is cooled to 0° C. and 10 percent by mass sulfuric acid is added dropwise until the pH value of the aqueous phase reaches 2.5. The organic phase is separated, the aqueous phase is extracted 4 times with 2o ml of ethyl acetate each, then the organic. solutions are combined, extracted with 30 ml of water, dried over anhydrous magnesium sulfate and evaporated under reduced pressure to obtain 13.9 g /95.8%/ of /2S/-methyl-3-thiocyantopropionic acid, $[\alpha]_D^{25} = -68°/c=1$; chloroform/.

The extracted aqueous phases remaining from the steps under A/ and B/ above are combined and rendered alkaline by adding 20 percent by mass aqueous sodium hydroxide solution, then extracted 3 times with 200 ml of benzene each. The organic solutions are combined, dried over anhydrous magnesium sulfate and evaporated. In this way about 90 percent of the /αS/-methylbenzomethane amine used can be recovered.

1-[/2S/-Methyl-3-thiocyanatopropionyl]-pyrrolidine- /2S/-carboxylic acid 29.4 g of /2S/-methyl-3-thiocyanatopropionic acid are dissolved in 400 ml of dichloromethane. To the solution cooled to −10° C. 17.38 g of pyridine are added, drop by drop, then 30.05 g of isobutyl chloroformate are added in 10 minutes. The suspension obtained is stirred at −5° to −10° C. for 10 minutes, then 23.06 g of L-proline and in 5 minutes 15.8 g of pyridine are added. The suspension is maintained at −5° C. for 1 hour, then let to reach room temperature, 300 ml of water are added, cooled to 0° C. and the pH value is adjusted to 1 by the addition of 10 percent by mass sulfuric acid.

The organic layer is separated, the aqueous phase is 4 times extracted with 400 ml of methylene chloride each. The organic solutions are combined, extracted with 400 ml of water, dried over anhydrous magnesium sulfate and evaporated under reduced pressure. To the residue 50 ml of ether are added, the crystal mass formed is maintained at 0° C. for some hours, then separated by filtration and washed with cold benzene to obtain 29.13 g /60.1%/ of the title product, m.p.: 135°–136° C.; $[\alpha]_D^{20} = -266.4°/c=1$; chloroform/.

IR spectra /KBr/ $\nu$ cm$^{-1}$: 2153 /NCS/, 1727 /CO, acid/.

We claim:

1. A process for the preparation of 1-[/2S/-methyl-3-mercaptopropionyl]-pyrrolidine-/2S/-carboxylic acid of the formula I

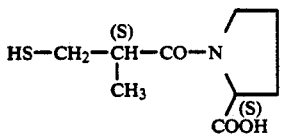

in which 1-[/2S/-methyl-3-thiocyanatopropionyl]-pyrrolidine-/2S/-carboxylic acid of the formula II

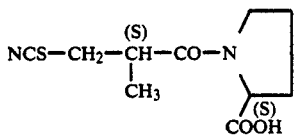

is dissolved in an aqueous mineral acid, the solution obtained is diluted with water and the 1-[/2S/-methyl-3-carbamoylthiopropionyl]-pyrrolidine-/2S/-carboxylic acid of the formula III

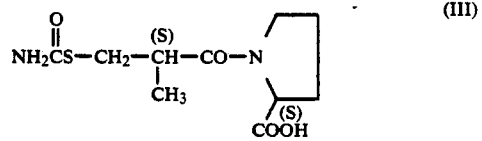

that forms is hydrolized with an aqueous solution of a base.

2. A process as claimed in claim 1, in which the mineral acid is sulfuric acid.

3. A process as claimed in claim 1, in which the 1-[/2S/-methyl-3-carbamoylthiopropionyl]-pyrrolidine-/2S/-carboxylic acid is at first separated, then hydrolized with the base.

4. A process as claimed in claim 1, in which the aqueous solution of a base is aqueous ammonia.

5. A process a claimed in claim 2, in which the 1-[/2S/-methyl-3-mercapto-propionyl]-pyrrolidine-/2s/-carboxylic acid is at first separated, then hydrolyzed with the base.

6. A process as claimed in claim 2, in which the aqueous solution of a base is aqueous ammonia.

7. A process as claimed in claim 3, in which the aqueous solution of a base is aqueous ammonia.

* * * * *